(12) United States Patent
Hasse et al.

(10) Patent No.: US 8,475,425 B2
(45) Date of Patent: Jul. 2, 2013

(54) TAMPON WITH CLEAN APPEARANCE POST USE

(75) Inventors: Margaret Henderson Hasse, Wyoming, OH (US); Steven Ray Gilbert, Fairfield, OH (US); James Earl Trout, West Chester Township, OH (US); Jared John Schaefer, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 526 days.

(21) Appl. No.: 12/055,532

(22) Filed: Mar. 26, 2008

(65) Prior Publication Data

US 2008/0177241 A1    Jul. 24, 2008

Related U.S. Application Data

(63) Continuation of application No. 10/653,836, filed on Sep. 3, 2003.

(60) Provisional application No. 60/408,455, filed on Sep. 5, 2002.

(51) Int. Cl.
*A61F 13/20* (2006.01)

(52) U.S. Cl.
USPC .................................... 604/385.18; 604/904

(58) Field of Classification Search
USPC ............................................ 604/385.18, 904
See application file for complete search history.

(56) References Cited

U.S. PATENT DOCUMENTS

| 3,055,369 | A |   | 9/1962  | Graham |
| 3,683,912 | A |   | 8/1972  | Olson et al. |
| 3,815,601 | A | * | 6/1974  | Schaefer ........................ 604/15 |
| 3,929,135 | A |   | 12/1975 | Thompson |
| 4,020,841 | A |   | 5/1977  | Poncy et al. |
| 4,211,225 | A | * | 7/1980  | Sibalis ..................... 604/385.18 |
| 4,863,450 | A |   | 9/1989  | Friese |
| 5,153,971 | A |   | 10/1992 | Van Iten |
| 5,374,258 | A |   | 12/1994 | Lloyd et al. |
| 5,533,990 | A |   | 7/1996  | Yeo |
| 5,814,330 | A |   | 9/1998  | Putterman et al. |
| 5,817,077 | A |   | 10/1998 | Foley |
| 5,827,256 | A |   | 10/1998 | Balzar |
| 6,186,995 | B1 |  | 2/2001  | Tharpe, Jr. |

(Continued)

FOREIGN PATENT DOCUMENTS

| EP | 0 685 215 A1 | 12/1995 |
| EP | 0 922 445 A2 | 6/1999 |

(Continued)

OTHER PUBLICATIONS

PCT Search Report, mailed Dec. 17, 2003, 5 pages.

(Continued)

*Primary Examiner* — Lynne Anderson
(74) *Attorney, Agent, or Firm* — Andrew J. Hagerty

(57) ABSTRACT

A catamenial tampon comprises a compressed absorbent member having an inner region and an exterior surface, the compressed absorbent member comprising an absorbent material. An overwrap substantially covers the exterior surface of the compressed absorbent member. The overwrap comprises an apertured fluid pervious material that is hydrophobic or rendered hydrophobic relative to the compressed absorbent member. The fluid pervious overwrap therefore tends to remain free of fluid as the fluid is preferentially partitioned into the absorbent member.

13 Claims, 1 Drawing Sheet

U.S. PATENT DOCUMENTS

| | | |
|---|---|---|
| 6,191,341 B1 | 2/2001 | Shippert |
| 6,299,573 B1 | 10/2001 | Hull et al. |
| 6,403,858 B1 | 6/2002 | Quincy, III |
| 6,465,713 B1 | 10/2002 | Gell et al. |
| 6,570,055 B2 | 5/2003 | Yang et al. |
| 6,719,743 B1 | 4/2004 | Wada |
| 6,840,927 B2 * | 1/2005 | Hasse et al. ............. 604/385.18 |
| 6,860,874 B2 | 3/2005 | Gubernick et al. |
| 7,214,219 B2 * | 5/2007 | Intravartolo et al. ..... 604/385.18 |
| 7,977,532 B2 | 7/2011 | Hasse et al. |
| 2001/0014348 A1 * | 8/2001 | Schoelling ................... 424/431 |
| 2002/0120246 A1 | 8/2002 | Buzot |
| 2002/0133135 A1 | 9/2002 | Gell et al. |
| 2002/0142693 A1 * | 10/2002 | Buzot ......................... 442/414 |
| 2002/0147436 A1 | 10/2002 | Gell et al. |
| 2003/0125687 A1 * | 7/2003 | Gubernick et al. ........... 604/383 |

FOREIGN PATENT DOCUMENTS

| | | |
|---|---|---|
| EP | 1 138 823 B1 | 6/2003 |
| JP | 62-144656 | 10/1992 |
| JP | 62-144657 | 10/1992 |
| JP | 08-141014 U | 6/1996 |
| JP | 11-155902 | 6/1999 |
| WO | WO 99/00096 A1 | 1/1999 |
| WO | WO 99/27878 A1 | 6/1999 |
| WO | WO 99/32061 A1 | 7/1999 |
| WO | WO 01/01905 A1 | 1/2001 |
| WO | WO 01/01909 A1 | 1/2001 |
| WO | WO 01/01910 A1 | 1/2001 |
| WO | WO 03/043555 A2 | 5/2003 |
| WO | WO 03/043556 A2 | 5/2003 |
| WO | WO 03/043557 A1 | 5/2003 |

OTHER PUBLICATIONS

US 6,353,147, 03/2002, Foley (withdrawn)

* cited by examiner

TAMPON WITH CLEAN APPEARANCE POST USE

CROSS REFERENCE TO RELATED APPLICATIONS

This application is a continuation of U.S. Ser. No. 10/653,836, filed Sep. 3, 2003, which claims the benefit of U.S. Provisional Application No. 60/408,455, filed Sep. 5, 2002.

FIELD OF THE INVENTION

This invention relates to an improved absorbent catamenial tampon having improved appearance after use.

BACKGROUND OF THE INVENTION

A wide variety of absorbent catamenial tampons have long been known in the art. While it has been found that these tampons perform their intended function well, the post use appearance of these tampons can have a negative impact on the user. Until recently it was not appreciated that the visual impact on the user of the post-use tampon was an important design criteria for tampons. In fact, it has been discovered that the post-use appearance is an important factor to consider in affecting the user's total use experience.

Accordingly, it would be beneficial to have a tampon that provides an improved visual appearance after use.

Further, it would be beneficial to have a tampon that, in addition to providing an improved appearance.

Finally, it would be beneficial to provide a tampon that can provide an improved appearance after use, and is economical to produce.

SUMMARY OF THE INVENTION

A catamenial tampon is disclosed. The tampon comprises a compressed absorbent member having an inner region and an exterior surface, the compressed absorbent member comprising an absorbent material. An overwrap substantially covers the exterior surface of the compressed absorbent member. The overwrap comprises an apertured fluid pervious material that is hydrophobic or rendered hydrophobic relative to the compressed absorbent member. The fluid pervious overwrap therefore tends to remain free of fluid as the fluid is preferentially partitioned into the absorbent member.

Apertures in the overwrap contribute to better fluid acquisition of fluid, including viscous fluid components of menses, by providing unimpeded fluid pathways to and into the absorbent member. By providing for preferential fluid paths into the absorbent member, the overwrap can remain relatively free of fluid, particularly viscous fluid, or fluid having solids components, again, such as menses. Therefore, the fluid pervious, apertured overwrap contributes to an overall cleaner post-use appearance.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying drawings, in which:

DETAILED DESCRIPTION OF THE INVENTION

Figure 1:
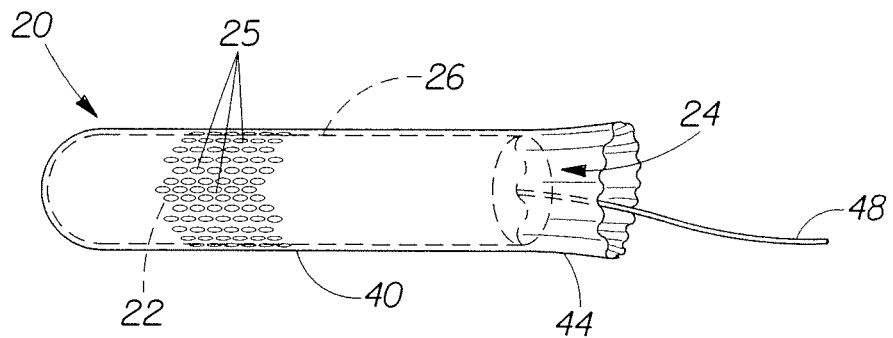
FIG. 1 is a perspective view of a tampon of the present invention incorporating a compressed absorbent member and fluid pervious overwrap covering the exterior surface.

The present invention comprises a fluid pervious overwrap that covers the exterior surface of a compressed absorbent member and which exhibits improved visual appearance after use. The overwrap can substantially permeate the folds and interstices, i.e., an inner region, of the compressed absorbent member and, as well, can extend beyond the withdrawal end to form a skirt.

The fluid pervious overwrap can comprise a fibrous nonwoven material. In one embodiment the nonwoven material can be apertured. The nonwoven material can comprise natural fibers, synthetic fibers, or a blend of synthetic and natural fibers that permit fluid to pass through to an absorbent member. The nonwoven material can be hydrophilic or hydrophobic. In a preferred embodiment, the nonwoven material is hydrophobic, or rendered hydrophobic.

The fluid pervious material can be used as is, or it can be apertured by methods known in the art to be an apertured, fluid pervious material. Apertures permit relatively viscous fluid, or fluid having some solids content, such as menses, to pass relatively unimpeded through the fluid pervious material such that it can be readily absorbed by the absorbent member. The apertures permit the fluid, such as menses, to penetrate deeper into the article to improve the masking property of the article. This is believed to be due to the absorbed fluid being offset a certain distance from the surface of the overwrap.

Therefore, the fluid pervious, preferably nonwoven, overwrap of the present invention permits fluid absorption into the compressed absorbent member. As well, in a preferred embodiment the fluid pervious overwrap is hydrophobic, or rendered hydrophobic, such that absorbed fluid is attracted to, and remains in, the absorbent member, not in the overwrap. Because of the relatively poor wicking propensity of the hydrophobic overwrap, the overwrap remains relatively free of menses, giving a cleaner visual appearance to the post-use article. In one embodiment, apertures provide for improved fluid flow into the core, and better visual appearance post use. By providing apertures in the overwrap, fluid absorption of relatively viscous fluid can be enhanced due to the lack of any obstruction to fluid absorption via the apertures. Post-use, the absorbent member is visible through the apertures and appears red. The overwrap remains relatively free of menses, and appears less soiled and closer to its original appearance. This gives the appearance of "deep down" menses storage, and overall cleanliness.

As used herein the term "tampon" refers to any type of absorbent structure that is inserted into the vaginal canal for the absorption of fluid therefrom. Typically, tampons are constructed from an absorbent material that has been compressed into a vaginally insertable shape.

As used herein the terms "pledget" or "tampon pledget" are intended to be interchangeable and refer to a construction of absorbent material prior to the compression of such construction into a tampon.

As used herein the terms "vaginal cavity," "within the vagina" and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule.

The externally visible genitalia generally is not included within the term "vaginal cavity" as used herein.

As used herein "fluid pervious" refers to the property of a material and is characterized by the ability to carry fluid or moisture, such as by capillary action, prior to any post-processing step, such as aperturing. Therefore, for example, an untreated woven or nonwoven material is fluid pervious and a thermoplastic film is not. A nonwoven permits fluid flow via the interstices between fibers, such that fluid can flow through, either by capillary action and/or via a pressure differential from one side of the nonwoven to the other such as the pressure experienced by a tampon in use.

As used herein "aperture" refers to a macroscopic opening or "hole" as distinct from inherent pores or interstices of fluid pervious materials, such as foams or nonwoven materials, for example. A macroscopic opening is visibly distinct to the naked eye of an observer having 20/20 vision at a distance of 45 cm.

As used herein "fluid pervious overwrap" refers to the fluid pervious material covering the exterior surface of the compressed absorbent member, as well as any interior surfaces or interior regions due to the folding or rolling of the pledget prior to compression. The portion of the fluid pervious overwrap disposed in the folds of the compressed absorbent member are said to substantially permeate the inner region of the compressed absorbent member. The fluid pervious overwrap can comprise a fibrous nonwoven material comprising natural, synthetic, or a blend of natural and synthetic fibers. The synthetic fibers can include but are not limited to fibers such as polyester, polyolefin, nylon, polypropylene, polyethylene, polyacrylic, cellulose acetate or bicomponent fibers. Natural fibers can include but are not limited to rayon and those commonly known to be non-synthetic and of natural origin such as cotton.

As used herein "hydrophilic" and "hydrophobic" have meanings as well established in the art with respect to the contact angle of a drop of water on the surface of a material. Thus, a material having a contact angle of greater than about 75 degrees is considered hydrophobic, and a material having a contact angle of less than about 75 degrees is considered hydrophilic. Absolute values of hydrophobocity/hydrophilicity are not generally important, but relative values are. Thus, the absorbent member of the tampon of the present invention is more hydrophilic than the overwrap, and the overwrap is more hydrophobic than the absorbent member.

As used herein the term "highly hydrophobic" refers to a material that has, or is rendered to have, a contact angle of 90 degrees.

As used herein "compressed" refers to pressing or squeezing together to change the size, shape, and/or volume to obtain a tampon having a vaginally insertable shape.

As used herein, "vaginally insertable shape" refers to the geometrical form of the absorbent tampon after compression. The tampon may be compressed into a generally cylindrical configuration in the radial direction along the longitudinal and/or lateral axes, axially, or in both the radial and axial directions. An example of a typical compressed tampon is one which is about 10-16 mm wide and about 30-55 mm long depending on absorbency. While the tampon may be compressed into a substantially cylindrical configuration, other shapes are possible. These may include shapes having a cross section that may be described as rectangular, triangular, trapezoidal, semi-circular, hourglass, or other suitable shapes.

Unless specifically stated otherwise, as used herein a first material is "substantially covering" or "substantially covers" a second material when the first material covers at least about 75%, typically at least about 90% of the surface area of the second material.

As used herein "substantially permeating" or "substantially permeates" refers to the manner in which the fluid pervious overwrap is positioned in relation to the inner region of the compressed absorbent member. For example, the fluid pervious overwrap can follow the spiral (in the case of rolled) or serpentine (in the case of the folded) contours of a compressed absorbent member and thereby extends into the inner region of said member along the interstices formed by the contours of the rolls or folds positioned in relation to the inner region of the compressed absorbent member. Any other compression method resulting in the fluid pervious overwrap similarly following the contours of the compressed absorbent member within the inner region is also acceptable.

The term "joined" or "attached" as used herein, encompasses configurations in which a first element is directly secured to second element by affixing the first element directly to the second element; configurations in which the first element is indirectly secured to the second element by affixing the first element to intermediate member(s) which in turn are affixed to the second element; and configurations in which first element is integral with second element; i.e., first element is essentially part of the second element.

The term "rolled" as used herein, is the configuration of the compressed absorbent member after winding the absorbent material substantially covered by the fluid pervious overwrap in a spiral round and round upon itself.

The term "folded" as used herein, is the configuration of the compressed absorbent member that may be incidental to lateral compaction of the absorbent material substantially-covered by the overwrap or may purposely occur prior to a compression step. Such a configuration is readily recognizable, for example, when the absorbent material abruptly changes direction such that one part of the absorbent material bends and lies over another part of the absorbent material.

As used herein, "cm" is centimeter, "mm" is millimeters, "ml" is milliliters "g" is grams, "gsm" is grams per square meter, "sec" is seconds.

FIG. 1 shows one embodiment of an absorbent tampon 20 of the present invention. A compressed absorbent member 22 (sometimes referred to as the "absorbent core") of the tampon 20 has an exterior surface 26. The compressed absorbent member 22 has an inner region 24. The exterior surface 26 of the compressed absorbent member 22 is substantially covered by a fluid pervious overwrap 40. The fluid pervious overwrap 40 can comprise a plurality of apertures 25 that permit improved fluid flow of viscous fluid to and into the compressed absorbent member 22. The fluid pervious overwrap can also extend to provide a skirl portion 44. In one embodiment, the tampon 20 includes a withdrawal means 48, such as a string.

The fluid pervious overwrap 40 is hydrophobic relative to the compressed absorbent member 22. Hydrophobicity can be inherent due to the material properties of the fluid pervious overwrap material, or the fluid pervious overwrap can be rendered hydrophobic by suitable treatment of an otherwise hydrophilic material. For example, the fluid pervious overwrap 40 can comprise a nonwoven web of conjugate fibers, such as bicomponent polyethylene/polypropylene fibers that are inherently more hydrophobic than the compressed absorbent member 22. Other hydrophobic fibers can also be used, such as bicomponent polyethylene/polyester fibers.

If the fluid pervious overwrap 40 comprises a nonwoven web material of hydrophilic fibers, such as rayon or a blend of rayon/cotton, the material can be rendered hydrophobic by a suitable treatment, such as a coating of a suitable material sufficient to render the fluid pervious overwrap sufficiently hydrophobic. For example, surface treatments can include applied coatings of silicone, such as Dow Corning 108® silicone, available from the Dow Corning Co. Inc., Midland Mich.; or Sucrose Esters of Fatty Acids (SEFA), available from the Procter & Gamble Co., Inc., Cincinnati, Ohio, polyolefin waxes, or NALAN® available from DuPont, Wilmington Del. Such coatings can render the fluid pervious overwrap hydrophobic, or highly hydrophobic. The application of a suitable surface treatment can be achieved by spraying, slot coating, immersion and other methods known in the art. The amount of coating can be varied as needed to render the fluid pervious overwrap 40 sufficiently hydrophobic relative to compressed absorbent member 22. In one embodiment, a 1% by weight coating of SEFA was found to be sufficient. Sufficient relative hydrophobicity is achieved when fluid such as menses is absorbed into the compressed absorbent member 22 in use, and is sufficiently desorbed from the fluid pervious overwrap 40 so as to partition the fluid into the core and away from the overwrap.

Figure 2:
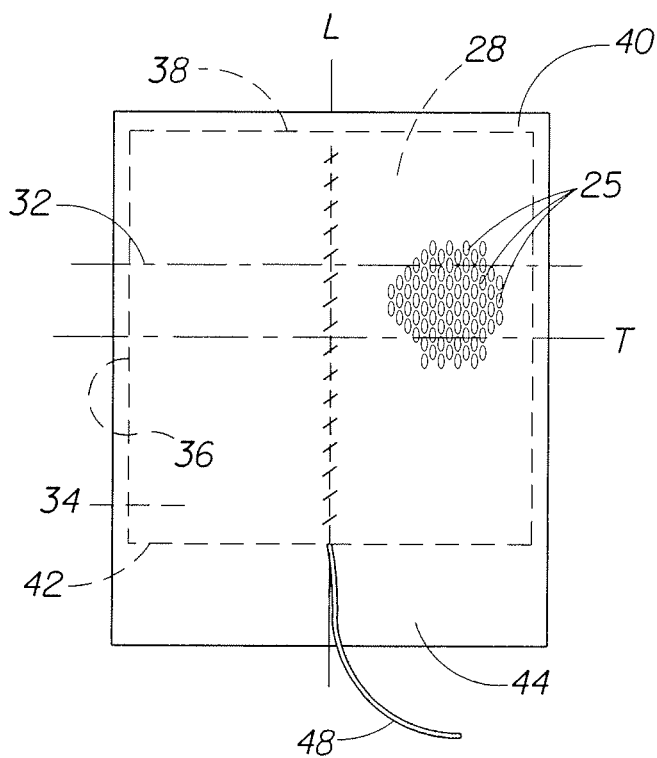
FIG. 2 is a plan view the assembled absorbent material and fluid pervious overwrap prior to compression.

FIG. 2 shows the absorbent tampon 20 in a flat-out configuration, prior to folding or rolling and compressing into the configuration shown in FIG. 1. Fluid pervious overwrap 40, shown in FIG. 2 as having a portion that is apertured, substantially covers the absorbent material 28 and preferably covers all of absorbent material 28. The absorbent material 28 has a first surface 34 opposed to a second surface 36 and an insertion end 38 opposed to a withdrawal end 42. The absorbent material 28 has both a longitudinal axis and a transverse axis indicated by the lines marked "L" and "T" respectively. Because the fluid pervious overwrap 40 can be wrapped in various configurations, the width (or length) of fluid pervious overwrap 40 may vary. The dimensions of the fluid pervious overwrap 40 may be greater than, lesser than, or equal to the dimensions of the longitudinal or transverse axes of the absorbent material being wrapped.

At least a portion of, and preferably all of, both first surface 34 and opposed second surface 36 of the absorbent material 28 is covered by fluid pervious overwrap 40 prior to compressing into compressed absorbent member 22. The fluid pervious overwrap can be positioned by folding around the insertion end 38 of the absorbent material 28. The fluid pervious overwrap can overlap at the region 32, for example. The overlapping portions in region 32 need not be sealed, partially sealed, or otherwise joined, although such joining can be done.

To form the compressed absorbent member 22, absorbent material 28 and fluid pervious overwrap 40 (shown in FIG. 2) is typically rolled or folded, compressed and optionally heat conditioned in any suitable conventional manner. After rolling or folding and compression, apertured fluid pervious overwrap 40 not only covers the exterior surface 26 of compressed absorbent member 22, but is also embedded in the interior folds of the compressed absorbent member 22. That is, the apertured fluid pervious overwrap permeates the interior of the compressed absorbent member 22.

The fluid pervious overwrap may be joined to the absorbent material by any variety of means. The fluid pervious overwrap may be joined to itself or to the absorbent material. For example, one portion of fluid pervious overwrap may be joined to an opposed portion of the fluid pervious overwrap or the absorbent member using any suitable adhesive or heat/pressure bonding means. Such adhesive may extend continuously along the length of attachment or it may be applied in a non-continuous fashion at discrete intervals. Heat bonding includes thermally bonding, fusion bonding, or any other suitable means known in the art for joining such materials. Alternatively, the fluid pervious overwrap may be joined to the absorbent material along with the withdrawal cord by stitching as shown in FIG. 2. Such stitching may use natural or synthetic thread.

Fluid pervious overwrap 40 can be made by any number of known techniques, but is preferably an apertured nonwoven material. The nonwoven material can be made by carding, meltblowing, spunbonding, spunlacing, air laying, and the like. Aperturing can be accomplished by any known method, such as by hydroentangling on a suitable forming screen, such as, for example, the method described in U.S. Pat. No. 3,025,585. Aperturing can also be accomplished by various processes involving bonding and stretching, such as those described in U.S. Pat. Nos. 3,949,127; 4,588,360; 5,873,868. In one embodiment, the apertures are formed by forming a plurality of spaced, melt stabilized regions, and then ring-rolling the web to stretch the web and form apertures in the melt stabilized regions, as described in U.S. Pat. Nos. 5,628,097 and 5,916,661, both of which are hereby incorporated by reference herein. In another embodiment, apertures can be formed in a multilayer overwrap by the method described in U.S. patent application Ser. No. 09/886,730 filed Jun. 21, 2001 in the name of Curro et al. and which is hereby incorporated herein by reference. In such a multilayer overwrap the outermost layer can be hydrophobic while the innermost layer can be hydrophilic. Other combinations of layers having various properties beneficial to the use of the overwrap can be made as desired.

Apertures 25 can be of virtually any shape and size, as long as the overwrap can provide the function of covering the absorbent member after in-use expansion, and provide for a masking effect after use. In a preferred embodiment, apertures 25 are generally round or oblong shaped, in a regular pattern of spaced apart openings. The apertures can each have a diameter of from 0.5 to 2 mm, preferably about 1 mm, and can form an open area of between 1% and 25%, preferably between 2% and 20%, most preferably between about 10% and 15%. It is believed that the benefits of the present invention can be realized with non-repealing and/or non-regular patterns of apertures having various shapes and sizes.

The basis weight of the nonwoven overwrap prior to forming apertures can be from about 10 to about 60 grams per square meter (gsm), alternatively from about 15 to about 30 gsm. Synthetic fibers, if used, may have hydrophobic and/or hydrophilic finishes, although, as mentioned above, the fibers of the nonwoven are preferably rendered hydrophobic relative to the absorbent member.

Therefore, in one embodiment, the present invention can be described as a catamenial tampon comprising a compressed absorbent member 22 having an inner region 24 and an exterior surface 26, the compressed absorbent member comprising an absorbent material. A fluid pervious overwrap substantially covers the exterior surface of the compressed absorbent member. The overwrap comprises a material that is hydrophobic or rendered hydrophobic relative to the compressed absorbent member.

In another embodiment, apertures 25 contribute to better fluid acquisition of viscous fluid components of menses by providing unimpeded fluid pathways to and into the absorbent member 22. By providing for preferential fluid paths into absorbent member 22, the overwrap 40 can remain relatively free of fluid, particularly viscous fluid, or fluid having solids components, again, such as menses. Therefore, the fluid pervious, apertured overwrap contributes to an overall cleaner post-use appearance.

Therefore, in one embodiment, the present invention can be described as a catamenial tampon comprising a compressed absorbent member 22 having an inner region 24 and an exterior surface 26, the compressed absorbent member comprising an absorbent material. An apertured fluid pervious overwrap substantially covers the exterior surface of the compressed absorbent member. The overwrap comprises a material that is hydrophobic or rendered hydrophobic relative to the compressed absorbent member.

The overwrap 44 is preferably biodegradable, or bio-disentegratable. Therefore, the fluid pervious overwrap 44 can comprise rayon, a rayon/cotton blend, or a blend of rayon and cotton with polymeric fibers, as is known in the art for biodegradable nonwoven webs. The rayon or rayon/cotton blend is then treated as discussed above to be hydrophobic.

The absorbent material 28 may be any suitable size and thickness suitable for compression into a tampon having a vaginally insertable shape. In the embodiment shown in FIG. 2, the absorbent material is generally square or rectangular, but other shapes such as trapezoidal, triangular, hemispherical, chevron and hourglass shaped are also acceptable. A typical size for absorbent material prior to compression can be from about 30 mm to about 100 mm in length and from about 30 mm to about 80 mm in width. The typical range for the overall basis weight of the absorbent material 28 is from about 150 gsm to about 1250 gsm depending upon desired absorbent capacity.

The absorbent material may be a laminar structure comprised of integral or discrete layers. In other embodiments, the pad need not have a layered structure at all. The absorbent material may comprise a folded structure or may be rolled. The resulting compressed absorbent member 22 of the tampon 20 may be constructed from a wide variety of liquid-absorbing materials commonly used in absorbent articles such as rayon (including tri-lobal and conventional rayon fibers), cotton, or comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these.

Typical absorbent materials comprise cotton, rayon folded tissues, woven materials, non-woven webs, synthetic and/or natural fibers or sheeting. The tampon and any component thereof may comprise a single material or a combination of materials. Additionally, superabsorbent materials, such as super polymers or absorbent gelling and open-celled foams, materials may be incorporated into the tampon.

The materials for the tampon can be formed into a fabric, web, or batt that is suitable for use in the absorbent material by any suitable process such as airlaying, carding, wetlaying, hydroentangling, needling or other known techniques.

Pressures and temperatures, suitable for compression are well known in the art. Typically, the absorbent material and the fluid pervious overwrap are compressed in the radial direction and optionally axially by any means well known in the art. While a variety of techniques are known and acceptable for these purposes, a tampon compressor machine available from Hauni Machines, Richmond, Va., is suitable.

In one embodiment, the tampon of the present invention may comprise a withdrawal means. The withdrawal means could be joined to the tampon and graspable by the user for removal after use. The withdrawal means may be joined to at least the compressed absorbent member and extends beyond the withdrawal end. Any of the withdrawal means currently known in the art, such as string, may be used as a suitable withdrawal mechanism. In addition, the withdrawal means can take on other forms such as a ribbon, loop, tab, or the like. The withdrawal means may be integral with the absorbent material.

The withdrawal means may be attached in any suitable manner known in the art including sewing, adhesive attachment, or a combination of known bonding methods. The withdrawal means may be joined to any suitable location on the tampon.

While several methods of making the tampon of the present invention should be apparent to one of skill in the art in light of the disclosure herein, following is a description of one method of making a tampon of the present invention.

The process for making a tampon comprises the steps of providing an absorbent material 28 having a first surface opposed to a second surface and an insertion end opposed to a withdrawal end. An apertured fluid pervious overwrap 40 is wrapped or folded about absorbent material 28 to cover, or substantially cover, the first surface 34 and second surface 36. The apertured fluid pervious overwrap can extend beyond the withdrawal end of the absorbent material to form a skirt portion. A withdrawal means 48 such as a string can attached, such as by stitching, to the absorbent material. The wrapped absorbent with a skirt is rolled or folded and/or compressed to form a compressed absorbent member 22 having a vaginally insertable shape. Upon compression the fluid pervious overwrap substantially covers the exterior surface of the compressed absorbent member and permeates into the interstices of the inner region of the compressed absorbent member.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A catamenial tampon comprising:
   a compressed absorbent member having an inner region and an exterior surface, the compressed absorbent member comprising an absorbent material;
   an overwrap substantially covering the exterior surface of the compressed absorbent member, the overwrap comprising a fluid pervious nonwoven material, the nonwoven material comprising a first portion having a plurality of apertures, the apertures being distinct from inherent pores or intersticies of the nonwoven material and being provided in a pattern of spaced apart openings, the nonwoven material comprising a second portion that is non-apertured, wherein a section of the overwrap extends beyond an end of the compressed absorbent member to form a skirt, and wherein the second portion of the nonwoven material is provided on the skirt.

2. A tampon according to claim 1, wherein the overwrap is hydrophobic or rendered hydrophobic.

3. A tampon according to claim 1, wherein the pattern is regular.

4. A tampon according to claim 1, wherein the pattern is non-repeating.

5. A tampon according to claim 1, wherein the apertures are more than one size.

6. A tampon according to claim 1 wherein the apertures are more than one shape.

7. A tampon according to claim 1, wherein the apertures have a diameter of from about 0.5 to about 2 mm.

8. A tampon according to claim 1, wherein the apertures form an open area of from about 1% to about 25%.

9. A catamenial tampon comprising:
- a compressed absorbent member having an inner region and an exterior surface, the compressed absorbent member comprising an absorbent material;
- an overwrap substantially covering the exterior surface of the compressed absorbent member, the overwrap comprising a fluid pervious nonwoven material, the nonwoven material comprising an apertured portion having a plurality of apertures, the apertures being distinct from inherent pores or intersticies of the nonwoven material and being two or more sizes, the nonwoven material comprising a second portion that is non-apertured, wherein a section of the overwrap extends beyond an end of the compressed absorbent member to form a skirt, and wherein the second portion of the nonwoven material is provided on the skirt.

10. A tampon according to claim 9, wherein the overwrap is hydrophobic or rendered hydrophobic.

11. A tampon according to claim 9, wherein the apertures are more than one shape.

12. A tampon according to claim 9, wherein the apertures have a diameter of from about 0.5 to about 2 mm.

13. A tampon according to claim 9, wherein the apertures form an open area of from about 1% to about 25%.

* * * * *